United States Patent [19]

Burke

[11] Patent Number: 4,939,298

[45] Date of Patent: Jul. 3, 1990

[54] ISOMERIZATION OF CARBOXYLIC ACIDS

[75] Inventor: Patrick M. Burke, Wilmington, Del.

[73] Assignee: E. I. du Pont de Nemours and Company, Wilmington, Del.

[21] Appl. No.: 392,041

[22] Filed: Aug. 10, 1989

Related U.S. Application Data

[63] Continuation-in-part of Ser. No. 283,157, Dec. 12, 1988.

[51] Int. Cl.$^5$ .................... C07C 51/10; C07C 51/353
[52] U.S. Cl. .................................. 562/591; 562/517; 562/590
[58] Field of Search ....................... 562/517, 590, 591

[56] References Cited

U.S. PATENT DOCUMENTS

| | | | |
|---|---|---|---|
| 3,090,807 | 5/1963 | Illing et al. | 562/591 |
| 4,260,820 | 4/1981 | Knifton | 562/517 |
| 4,334,092 | 6/1982 | Knifton | 562/517 |

Primary Examiner—Werren B. Lone
Assistant Examiner—Vera C. Clarke

[57] ABSTRACT

Isomerization of branched saturated alkyl carboxylic acids to linear or isomeric branched alkyl carboxylic acids, or vice versa, by heating in the presence of a iodide or bromide promoted rhodium catalyst and carbon monoxide.

8 Claims, No Drawings

ISOMERIZATION OF CARBOXYLIC ACIDS

CROSS-REFERENCE TO RELATED APPLICATION

This application is a continuation-in-part of U.S. patent application Ser. No. 07/283,157 filed Dec. 12, 1988.

FIELD OF THE INVENTION

This invention relates to an improved process for the isomerization (interconversion) of linear and branched carboxylic acids.

1. Background of the Invention

Processes for the isomerization of $C_4$ to $C_{20}$ saturated carboxylic acids or anhydrides by heating in the presence of group 8 noble metal catalysts having phosphine, arsine or stilbine ligands are disclosed in U.S. Pat. Nos. 3,578,688 and 3,592,849.

In the preparation of dicarboxylic acids, by carbonylation of diolefins or olefinic acids, the reaction product often contains isomers of the desired dicarboxylic acid, but methods for the conversion of these isomers to the desired product have not been entirely satisfactory. For example, the prior art palladium catalysts having phosphine ligands are known to be unstable at the high temperatures required to produce satisfactory isomerization rates.

2. Summary of the Invention

The present invention is a process for the interconversion (isomerization) of branched and linear alkyl carboxylic acids having 4 to 20 carbon atoms and at least one hydrogen on a beta carbon atom. The carboxylic acid may be a monocarboxylic acid or a dicarboxylic acid. The conversion may be from a branched compound to a linear compound, or from a linear compound to a branched compound, or from a branched compound to an isomeric branched compound.

The interconversion takes place in the presence of an iodide or bromide promoted rhodium catalyst. The catalyst may be formed in-situ by adding a rhodium compound and a suitable iodine or bromine compound to the other components of the mixture to be reacted, or the promoted catalyst may be prepared prior to its addition to the mixture.

The compound to be isomerized is heated to a temperature in the range of 170° to 250° C. in the presence of carbon monoxide at a carbon monoxide pressure of 200 to 10,000 psi.

The isomerization may be carried out in a solvent for the compound being isomerized. Lower aliphatic acids are suitable, and acetic acid is satisfactory. Other solvents that may be used are aliphatic halides such as methylene chloride, aromatic solvents such as toluene and xylene, and polar aprotic solvents such as tetramethylene sulfone. No solvent is necessary if the compound to be isomerized is liquid under the conditions of reaction.

DETAILED DESCRIPTION

The process of this invention is an isomerization process involving a $C_4$ to $C_{20}$ saturated alkyl carboxylic acid. The carboxylic acid must have at least one hydrogen on a beta carbon atom. The beta carbon atom is the one marked with the asterisk in the formula

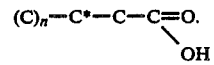

where n is 1 to 17.

The carboxylic acid may be branched or linear. A particularly preferred process involves the isomerization of branched $C_6$ acids to adipic acid, for example the isomerization of 2-methylglutaric acid or ethylsuccinic acid. However, the isomerization reaction can be just the reverse of the above, i.e., the conversion of adipic acid into 2-methylglutaric acid. The process of the invention will also isomerize monocarboxylic acids of 4 to 20 carbon atoms.

The iodide or bromide promoted rhodium catalyst can be made from a suitable rhodium compound, for example, any rhodium complex that is free of interfering ligands, particularly bidentate phosphine and nitrogen ligands. Rhodium complexes such as rhodium(III) chloride-$RhCl_3.3H_2O$, rhodium (III) iodide-$RhI_3$, rhodium carbonyliodide-$Rh(CO)_nI_3$ (n=2-3), rhodium(III) nitrate-$Rh(NO_3)_3.2H_2O$, dodecacarbonyltetrarhodium-(O)-$Rh_4(CO)_{12}$, acetylacetonatodicarbonylrhodium(I)-$Rh(CO)_2(C_5H_7O_2)$, chlorobis(ethylene)rhodium(I) dimer-$[Rh(C_2H_4)Cl]_2$, acetylacetonato(1,5-cyclooctadiene)rhodium(I)-$Rh(C_8H_{12})(C_5H_7O)_2$, chlorocarbonylbis(triphenylphosphine) rhodium(I)-$RhCl(CO)(PPh_3)_2$, hexadecacarbonylhexarhodium(0)-$Rh_6(CO)_{16}$, tris(acetylacetonato)rhodium(III)-$Rh(C_5H_7O_2)_3$, rhodium(II)octanoate dimer-$Rh_2[CO_2(CH_2)_6CH_3]_4$, chlorodicarbonylrhodium(I) dimer-$[Rh(CO)_2Cl]_2$, chloro(1,5-cyclooctadiene)rhodium(I)dimer-$[Rh(C_8H_{12})Cl]_2$, acetylacetonatobis(ethylene)rhodium(I)-$Rh(C_2H_4)_2(C_5H_7O_2)$ and rhodium(II)acetate dimer-$Rh_2(CO_2CH_3)_4$ are operable.

The concentration of iodide or bromide promoted catalyst is not critical but is usually maintained in the range 0.005–0.50%, preferably 0.05–0.15%, by weight of rhodium metal based upon the weight of the reaction medium. Stated in terms of the amount of rhodium employed per amount of compound to be isomerized—the ratio of 1 part by weight rhodium to 50 to 200 parts by weight of the compound to be isomerized is satisfactory. The weight of the reaction medium includes the weight of solvent, rhodium compound, promoter and reactants. Hydrogen iodides and hydrogen bromides are preferred promoters at the higher reaction temperatures. Other suitable promoters include alkyl iodides and alkyl bromides having 1 to 6 carbon atoms such as iodoethane, 1-iodobutane, 1,4-di-iodobutane, 2-iodopropane, 1-iodopropane and iodoheptane, and the corresponding bromine compounds. As believed apparent from the foregoing, the promoter and rhodium can be present in the same compound as in rhodium iodide. Generally the concentration of promoter is between 0.05-4.5% by weight iodide or bromine based upon the weight of the reaction medium and at a mole ratio to rhodium in the range 1/1 to 30/1, preferably 3/1 to 15/1.

Water is produced during the course of the reaction, and water, in the amount of up to about 50% by weight of the reaction mixture, is often a desirable component in the reaction mixture. Water may be added to the reaction mixture prior to or along with the iodide or bromide promoted rhodium catalyst, or along with the catalyst precursors, if the catalyst is to be formed in situ.

The amount of water in the reaction mixture may be controlled by adding a carboxylic acid anhydride.

In the following Examples all parts and percents are in parts by weight unless otherwise specified.

DETAILED EXAMPLE

EXAMPLE 1

Isomerization of 2-methylglutaric Acid (MGA) to Adiptic Acid: Hydrogen Iodide Promoter in Acetic Acid + Acetic Anhydride Solvent A 300 ml Hastelloy-C mechanically stirred autoclave was flushed with nitrogen and then with high purity carbon monoxide. It was then charged with 150 ml of an acetic acid solution containing 11.0 grams (75 mmole) of 2-methylglutaric acid (MGA), 6.73 grams 57% aq HI (30 mmole HI), 28 grams (275 mmole) acetic anhydride and 5.0 grams o-dichlorobenzene ODCB, (internal GC standard). The autoclave was pressured with CO to 500 psi and then heated to 220° C. The reaction was initiated by injecting into the autoclave a solution made by dissolving 0.8 grams (3 mmoles) $RhCl_3.3H_2O$ in 3.0 grams (150 mmole) water. The autoclave pressure was then immediately adjusted to 1000 psi with CO by means of a regulator valve. The reaction was allowed to run for a total of 5 hours after which it was cooled to 20° C. The excess CO was vented through a control valve and the product was discharged. The autoclave was washed first with 200 ml methanol at 100° C. under autogenous pressure and then with 150 ml methanol at room temperature.

The product and washes from the autoclave were combined, filtered and the filtrate was diluted to 500 ml with methanol. A sample of this solution was esterified by heating in a sealed vial at 90° C. for 14 hours with trimethylorthoformate and sulfuric acid esterification catalyst. It was analyzed as the methyl esters by capillary gas chromatography. The analysis showed the following composition (moles product per 100 moles MGA charged):

|  | Actual | Normalized |
|---|---|---|
| Adipic acid | 14.1% | 16.2% |
| Recovered 2-methylglutaric acid | 61.2% | 70.2% |
| Ethylsuccinic acid | 2.2% | 2.6% |
| γ-valerolactone | 3.4% | 3.9% |
| 2-pentenoic acid | 1.1% | 1.3% |
| valeric acid | 3.0% | 3.4% |
| 2-methylbutyric acid | 2.2% | 2.5% |
| Total | 87.2% | 100% |

Product accounting* was 87.2%, MGA conversion was 38.8% and adipic acid yield** was 36.3%.
*Moles of all products recovered divided by moles MGA charged × 100 (%)
**Moles of adipic acid formed per 100 moles MGA reacted (uncorrected for accounting losses)

EXAMPLE 2

Isomerization of 2-methylglutaric Acid to Adipic Acid: HI Promoter in Acetic Acid + Acetic Anhydride Solvent at Higher Temperature (240° C.)

The experiment in Example 1 was repeated except that the temperature was increased to 240° C. and the pressure was kept at 1000 psi. Analysis of the product showed 48% MGA converted, 11.3% adipic acid yield and 69.5% product accounting.

EXAMPLE 3

Isomerization of 2-methylglutaric Acid to Adipic Acid: Methyl Iodide-Methanol Promoter in Acetic Acid Solvent The experiment in Example 1 was repeated except that the autoclave was charged with 150 ml of an acetic acid solution containing 11.0 grams MGA, 4.16 grams (30 mmoles) methyl iodide, 0.96 grams (30 mmoles) methanol and 5.0 grams ODCB internal GC standard. Reaction was initiated by injecting at 220° C. and 500 psi a solution of 0.4 grams (1.5 mmoles) $RhCl_3.3H_2O$ in 1.5 grams (75 mmoles) water. The reaction was allowed to run for 5 hours at 220° C. and 1000 psi total pressure. GC analysis showed the following composition:

|  | Actual | Normalized |
|---|---|---|
| Adipic acid | 14.2% | 15.5% |
| Recovered 2-methylglutaric acid | 55.7% | 60.7% |
| Ethylsuccinic acid | 2.0% | 2.2% |
| γ-valerolactone | 8.6% | 9.3% |
| 2-pentenoic acid | 2.1% | 2.3% |
| valeric acid | 5.7% | 6.3% |
| 2-methylbutyric acid | 3.4% | 3.7% |
| Total | 91.7% | 100% |

The data show about 44% MGA conversion, 32% yield of adipic acid 92% product accounting.

EXAMPLE 4

Isomerization of 2-methylglutaric Acid to Adipic Acid: Methyl Iodide - Methanol Promoter in Acetic Acid Solvent at Lower Temperature (190° C.).

The experiment in Example 3 was repeated except that the temperature was decreased to 190° C., the reaction time was increased to 24 hours and the pressure was kept at 1000 psi. Analysis of the product showed 52% MGA converted and 30.4% adipic acid yield (product accounting was 70.7%).

EXAMPLE 5

Isomerization of 2-methylglutaric Anhydride to Adipic Acid: Methyl Iodide Promoter in Acetic Acid Solvent The experiment in Example 1 was repeated except that the reactor was charged with 150 ml of an acetic acid solution containing 9.6 grams (75 mmoles) of 2-methylglutaric anhydride, 2.13 grams (15 mmoles) methyl iodide, and 5.0 grams ODCB internal GC standard. Reaction was initiated by injecting at 220° C. a solution of 0.4 grams $RhCl_3.3H_2O$ in 6 ml water. Reaction was allowed to run at 220° C. and 400 psi total pressure for 5 hours. Analysis of the product showed

|  | Actual | Normalized |
|---|---|---|
| Adipic acid | 6.1% | 7.0% |
| 2-Methylglutaric acid | 53.3% | 61.1% |
| Ethylsuccinic acid | 12.3% | 14.1% |
| γ-Valerolactone | 5.3% | 6.1% |
| 2-Pentenoic acid | 3.1% | 3.6% |
| 3-Pentenoic acid | 3.2% | 3.7% |
| Valeric acid | 3.9% | 4.5% |
| 2-Methylbutyric acid | — | — |
| Total | 87.2% | 100% |

The data show about 47% MGA anhydride conversion and 14.9% adipic acid yield.

EXAMPLE 6

Isomerization of Adipic Acid to Branched Dicarboxylic Acids with Hydrogen Iodide Promoter in Acetic Acid Solvent A 75 ml Hastelloy-C shaker tube was charged with 5.84 grams (40 mmoles) adipic acid, 0.21 g $RhCl_3.3H_2O$ (0.8 mmoles), 1.82 g 57% aqueous HI (8 mmoles HI), 1.0 g ODCB (internal GC standard) and 38 ml acetic acid. The tube was closed, cooled to −78° C., evacuated and then pressured with carbon monoxide to a pressure of 300 psi. The tube was heated with agitation to 230° C. over about 40 minutes; the total initial pressure at 230° C. was about 700 psi. The temperature was maintained at 230° C. for a total of 5 hours. The final pressure was 765 psi. The tube was cooled to 0° C., and the excess CO pressure was slowly vented. The product was discharged and the tube was rinsed twice with 20 ml portions of methanol. The combined product and washings were made up to 100 ml with methanol. A sample of the product solution was esterified by heating at 90° C. for 14 hours with a large excess of methanol in the presence of a catalytic amount of p-toluenesulfonic acid. It was analyzed as the methyl esters on a 30m CP-Sil-19 capillary GC column. The analysis showed the following composition (moles product per 100 moles adipic acid charged):

|  | Actual | Normalized |
|---|---|---|
| Adipic acid | 58.3% | 57.5% |
| 2-Methylglutaric acid | 19.6% | 19.3% |
| Ethylsuccinic acid | 2.7% | 2.7% |
| γ-Valerolactone | 9.5% | 9.4% |
| 2-Pentenoic acid | 0.0% | 0.0% |
| 3-Pentenoic acid | 0.0% | 0.0% |
| Valeric acid | 9.1% | 9.0% |
| 2-Methylbutyric acid | 2.2% | 2.1% |
| Total | 101.4% | 100% |

The data show about 42.5% adipic acid conversion and 52% yield of branched acids.

EXAMPLE 7

Isomerization of MGA t Adipic Acid with Hydrogen Iodide Promoter in Acetic Acid Solvent The experiment in Example 6 was repeated except that the adipic acid was replaced with an equimolar amount of 2-methylglutaric acid. Analysis of the product gave the following results:

|  | Actual | Normalized |
|---|---|---|
| Adipic acid | 10.9% | 11.7% |
| 2-Methylglutaric acid | 69.2% | 74.1% |
| Ethylsuccinic acid | 1.6% | 1.8% |
| γ-Valerolactone | 4.6% | 9.4% |
| 2-Pentenoic acid | 0.2% | 0.2% |
| 3-Pentenoic acid | 0.0% | 0.0% |
| Valeric acid | 4.2% | 4.8% |
| 2-Methylbutyric acid | 2.6% | 3.0% |
| Total | 93.4% | 100% |

The data show about 30% MGA conversion and 35.4% yield of adipic acid.

EXAMPLE 8

Isomerization of Adipic Acid to Branched Acids with Hydrogen Bromide Promoter in Acetic Acid Solvent The experiment in Example 6 was repeated except that HI promoter was replaced with an equimolar amount of 48% aqueous HBr and the reaction was run at 220° C. and 200 psi initial cold CO pressure. The total pressure at 220° C. was 480 psi and the pressure after 5 hours at 220° C. was 588 psi. Analysis of the product gave the following results:

|  | Actual | Normalized |
|---|---|---|
| Adipic acid | 52.4% | 52.7% |
| 2-Methylglutaric acid | 26.0% | 26.1% |
| Ethylsuccinic acid | 3.8% | 3.8% |
| γ-Valerolactone | 6.7% | 6.7% |
| 2-Pentenoic acid | 0.7% | 0.7% |
| 3-Pentenoic acid | 0.0% | 0.0% |
| Valeric acid | 7.1% | 7.1% |
| 2-Methylbutyric acid | 2.8% | 2.8% |
| Total | 99.5% | 100% |

The data show about 48% adipic acid conversion and 62.6% yield of branched acids.

EXAMPLE 9

Isomerization of Valeric Acid to 2-methylbutyric Acid with Hydrogen Bromide Promoter in Acetic Acid Solvent The experiment in Example 6 was repeated except that the adipic acid was replaced with an equimolar amount of valeric acid, the HI promoter was replaced with an equimolar amount of 48% aqueous HBr (1.4 grams) and the reaction was run at 220° C. and 200 psi initial cold CO pressure. The total pressure at 220° C. was 475 psi and the pressure after 5 hours at 220° C. was 542 psi. Analysis of the product gave the following results:

| Valeric acid | 86.9% |
|---|---|
| 2-Methylbutyric Acid | 5.3% |

EXAMPLE 10

Isomerization of Valeric Acid to 2-methylbutyric Acid with Hydrogen Iodide Promoter in Acetic Acid/Acetic Anhydride Solvent The experiment in Example 6 was repeated except that the adipic acid was replaced with an equimolar amount of valeric acid, 4.1 grams (40 mmoles) acetic anhydride was added and the reaction was run at 230° C. and 300 psi initial cold CO pressure. The total pressure at 230° C. was 583 psi and the pressure after 5 hours at 230° C. was 583 psi. Analysis of the product gave the following results:

| Valeric acid | 57.8% |
|---|---|
| 2-Methylbutyric Acid | 26.4% |

EXAMPLE 11

Isomerization of 2-methylbutyric Acid to Valeric Acid with Hydrogen Iodide Promoter in Acetic Acid/Acetic Anhydride Solvent The experiment in Example 6 was repeated except that the adipic acid was replaced with an equimolar amount of 2-methylbutyric acid (4.1 grams), 4.1 grams acetic anhydride was added and the reaction was run at 230° C. and 300 psi initial cold CO pressure. The total pressure at 230° C. was 645 psi and the pressure after 5 hours at 230° C. was 653 psi. Analysis of the product gave the following results:

| Valeric acid | 14.3% |
| --- | --- |
| 2-Methylbutyric Acid | 84.9% |

EXAMPLE 12

Isomerization of MGA to Adipic Acid with Methyl Iodide Promoter in Methylene Chloride Solvent A 200 ml Hastelloy-C shaker tube was charged with 10.8 grams (74 mmoles) MGA, 0.19 g (0.7 mmoles) $RhCl_3.3H_2O$, 4.25 g (30 mmoles) methyl iodide, 0.5 g (30 mmoles) water and 75 ml methylene chloride. The tube was closed, cooled to $-78°$ C., evacuated and then pressured with carbon monoxide to 800 psi. The tube was heated with agitation to 180° C. over 60 minutes. The temperature was maintained at 180° C. for a total of 3 hours. The tube was cooled to 0° C., and the excess CO pressure was slowly vented. The product was discharged and the tube was rinsed with tetrahydrofuran. The combined product and washings were made up to 200 ml with tetrahydrofuran.

A sample of the product solution was derivatized by treating with an excess of bis(trifluoromethyl)acetamide. It was analyzed by gas chromatography on a QF-1/SE30 packed column as the trimethylsilyl esters. The analysis showed the following composition (moles product per 100 moles MGA charged):

| Adipic acid | 3.3% |
| --- | --- |
| 2-Methylglutaric acid | 96.0% |
| Ethylsuccinic acid | 0.7% |

No other products were present in significant amounts (>0.5%). The data show about 4% MGA conversion and 82.5% yield of adipic acid.

I claim:

1. A process for the isomerization of saturated alkyl carboxylic acids having 4 to 20 carbon atoms and having at least one hydrogen on a beta carbon atom, which comprises heating a reaction medium containing said saturated acid, a solvent for said saturated acid, an iodide or bromide promoted rhodium catalyst, and carbon monoxide to a temperature in the range of 170 to 250 degrees C. at a carbon monoxide pressure of 200 to 10,000 psi, where the amount of iodide or bromide promoted rhodium catalyst is in the range of 0.005 to 0.50% by weight of rhodium metal based on the weight of the reaction medium.

2. The process of claim 1 in which the rhodium catalyst is promoted by a compound selected from the class consisting of hydrogen iodide, hydrogen bromide, an alkyl iodide having 1 to 6 carbon atoms, and an alkyl bromide having 1 to 6 carbon atoms.

3. The process of claim 2 in which the water is present in the amount up to about 50% by weight of the reaction mixture.

4. The process of claim 3 in which said saturated acid is 2-methylglutaric acid and said saturated acid is isomerized to adipic acid.

5. The process of claim 1 in which the saturated acid is a dicarboxylic acid.

6. The process of claim 1 in which the saturated acid is ethylsuccinic acid and said saturated acid is isomerized to adipic acid.

7. The process of claim 1 in which the solvent is a lower aliphatic carboxylic acid.

8. The process of claim 7 in which the solvent is acetic acid.

* * * * *